(12) United States Patent
Baynham

(10) Patent No.: US 10,034,767 B2
(45) Date of Patent: Jul. 31, 2018

(54) SPINAL IMPLANT DEVICE

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 0 days.

(21) Appl. No.: 15/664,891

(22) Filed: Jul. 31, 2017

(65) Prior Publication Data

US 2018/0014947 A1    Jan. 18, 2018

Related U.S. Application Data

(63) Continuation-in-part of application No. 14/642,992, filed on Mar. 10, 2015, now Pat. No. 9,717,605, which is a continuation-in-part of application No. 14/294,889, filed on Jun. 3, 2014, now Pat. No. 9,445,920.

(51) Int. Cl.
*A61F 2/44* (2006.01)
*A61F 2/30* (2006.01)

(52) U.S. Cl.
CPC .. *A61F 2/4455* (2013.01); *A61F 2002/30261* (2013.01); *A61F 2002/30383* (2013.01); *A61F 2002/30537* (2013.01); *A61F 2002/30579* (2013.01); *A61F 2002/4475* (2013.01)

(58) Field of Classification Search
CPC . A61F 2/442; A61F 2/4425; A61F 2002/4435
USPC ............... 623/17.11–17.16; 606/246–249
See application file for complete search history.

(56) References Cited

U.S. PATENT DOCUMENTS

| | | |
|---|---|---|
| 8,556,979 B2 | 10/2013 | Glerum et al. |
| 2009/0292361 A1* | 11/2009 | Lopez ............... A61F 2/446 623/17.15 |
| 2011/0093074 A1 | 4/2011 | Glerum et al. |
| 2012/0226356 A1 | 9/2012 | Hirschl |
| 2013/0006361 A1 | 1/2013 | Glerum et al. |
| 2015/0342749 A1 | 12/2015 | Baynham |

* cited by examiner

*Primary Examiner* — Ellen C Hammond
*Assistant Examiner* — Christina Negrellirodrigue
(74) *Attorney, Agent, or Firm* — McHale & Slavin, P.A.

(57) ABSTRACT

A spinal fusion device that is expandable. The device features a top and bottom surface for engaging adjacent vertebrae, a hollow center for stacking of bone or bone growth material, and a slidable mechanism with grooves for expanding or contracting the device in cooperation with a hinge assembly.

19 Claims, 13 Drawing Sheets

SPINAL IMPLANT DEVICE

PRIORITY CLAIM

In accordance with 37 C.F.R. 1.76, a claim of priority is included in an Application Data Sheet filed concurrently herewith. Accordingly, the present invention claims priority as continuation-in-part of U.S. patent application Ser. No. 14/642,992, entitled "SPINAL IMPLANT DEVICE", filed Mar. 10, 2015, which is a continuation-in-part of U.S. patent application Ser. No. 14/294,889, entitled "SPINAL IMPLANT DEVICE", filed Jun. 3, 2014, now U.S. Pat. No. 9,445,920, issued on Sep. 20, 2016. The contents of the above referenced applications are incorporated herein by reference.

FIELD OF THE INVENTION

Embodiments of the invention relate to the field of orthopedic surgery, and more particularly, to implants to be placed between vertebrae in the spine.

BACKGROUND

Spinal stabilization is one approach to alleviating chronic back pain caused by disabled disk material or excessive movement of individual vertebrae. Conventional stabilization techniques include fusing two or more vertebrae together to circumvent or immobilize the area of excessive movement. Normally, the vertebral disk material which separates the vertebrae is removed and bone graft material is inserted in the space for interbody fusion. In addition to, or in place of, the bone graft material, a spinal implant may be inserted in the intervertebral space.

The conventional surgical approach for stabilization has been posteriorly for ease of access to the spine and to avoid interfering with internal organs and tissues. Usually, the implant site is prepared to maintain natural lordosis and to accept a certain sized implant within certain pressure limits. This requires considerable time and skill by the surgeon.

DESCRIPTION OF THE PRIOR ART

U.S. Pat. No. 8,556,979, issued Oct. 15, 2013, describes an expandable fusion device capable of being installed inside an intervertebral disc space to maintain normal disc spacing and restore spinal stability. The fusion device includes a body portion, a first end plate, and a second end plate; both of these end plates can be moved in a direction away from the body portion or towards the body portion into an unexpanded configuration.

SUMMARY OF THE INVENTION

Embodiments of the invention are directed to an expandable spinal fusion device comprising upper and lower sections with depending sidewalls forming a cube-like or rectangular structure with a hollow center. The upper and lower sections comprise a top and a bottom surface, respectively, for engaging adjacent vertebrae, a slidable mechanism for expanding or compacting the device, and a hollow center allowing for packing with bone graft or similar bone growth inducing material. The slidable mechanism comprises slots or grooves on each of the sidewalls depending from the top and bottom surfaces, and a distractor. The distractor comprises a rod, a body and an actuator for enabling distraction. The rod can be telescopic or a jack screw type rod. The distractor comprises a body with protruding members, rollers or pins, for engaging the grooves which are positioned in the exact location directly opposite from each other. When the distractor is actuated, the body slides upwards, downwards or sideways depending on the groove geometry.

The device is inserted between the adjacent vertebrae and expanded or increased in height to engage the opposing surfaces of the adjacent vertebra. The adjacent vertebrae are forced apart as the height of the implant increases. The spinal fusion device may be used unilaterally or bilaterally.

Accordingly, it is an objective of the instant invention to teach a posterior surgical approach for placement of an adjustable spinal implant for interbody fusion, allowing the implant to be inserted through a small incision and increased in size in situ.

It is another objective of the instant invention to teach a spinal implant which allows the surgeon to provide for lordosis intraoperatively and to distract through the implant.

It is yet another objective of the instant invention to teach an implant facilitating interbody fusion through bone graft or an ingrowth type implant.

Although embodiments are directed to posterior surgical approaches and to provide for lordosis intraoperatively, it is to be understood that the invention may be employed in cervical and thoracic spinal procedures, as well as from any direction, that is, anterior, posterior and lateral.

Other objectives and advantages of this invention will become apparent from the following description taken in conjunction with the accompanying drawings wherein are set forth, by way of illustration and example, certain embodiments of this invention. The drawings constitute a part of this specification, include exemplary embodiments of the present invention, and illustrate various objects and features thereof.

DETAILED DESCRIPTION

Figure 1:
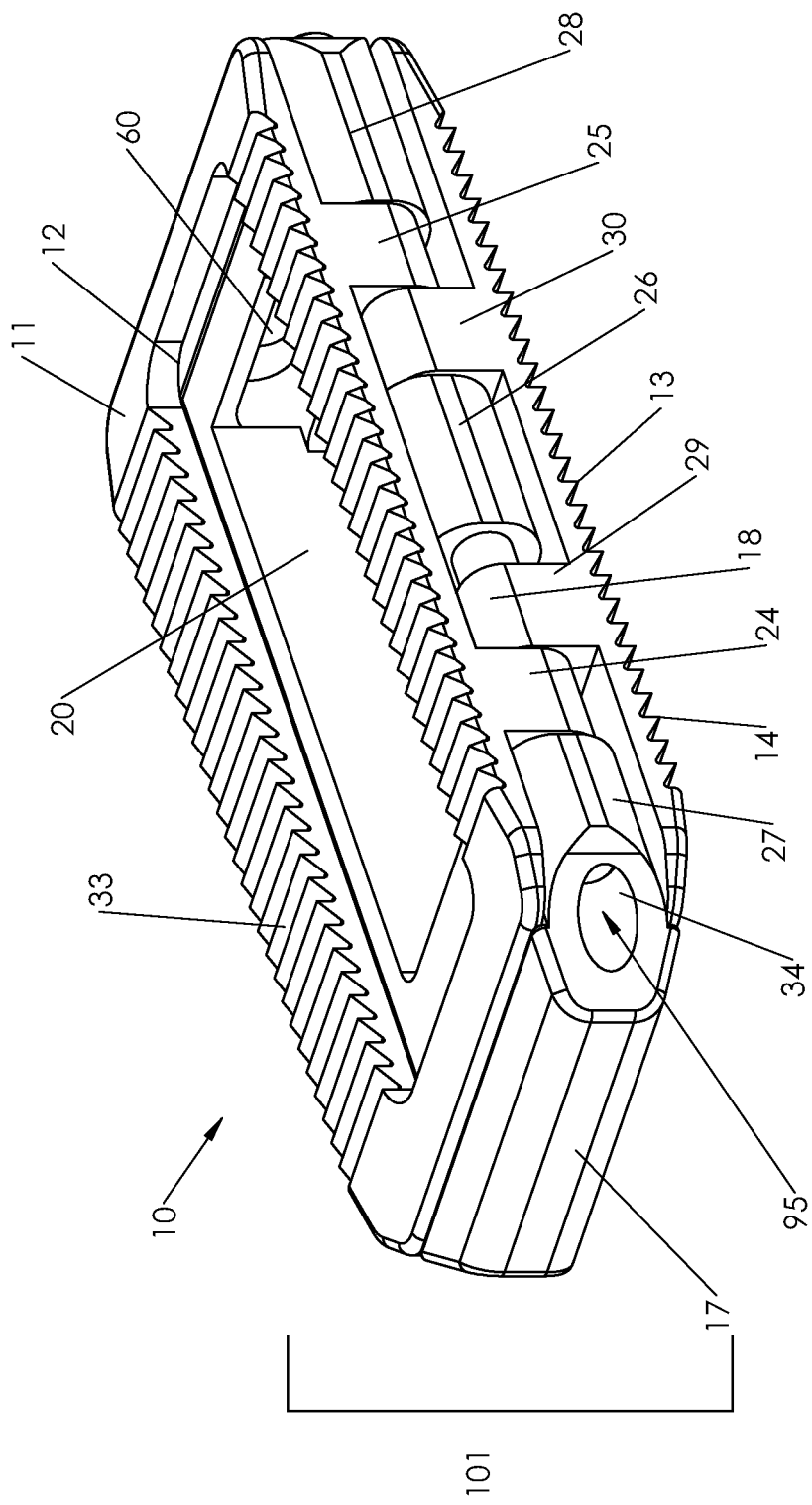
FIG. 1 is a perspective view of the spinal implant in a contracted position.
Figure 2:
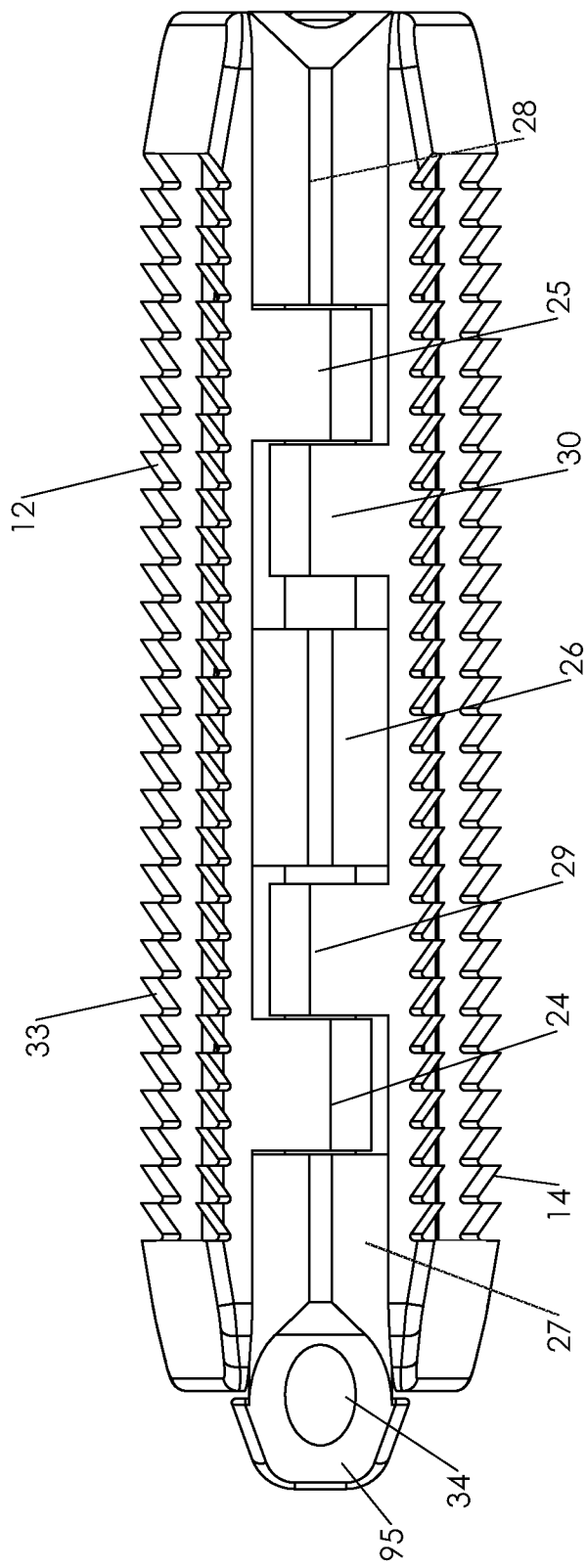
FIG. 2 is a side view of FIG. 1.
Figure 3:
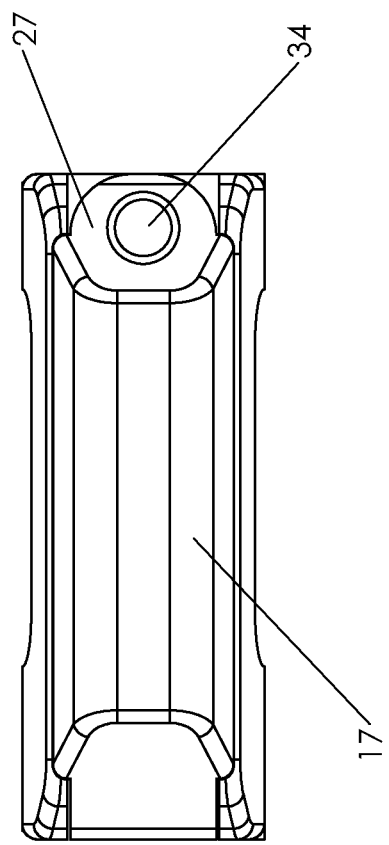
FIG. 3 is an end view of FIG. 1.

The following description of the preferred embodiments is merely exemplary in nature and is in no way intended to limit the invention, its application or uses.

It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the illustrated ordering of acts or events, as some acts may occur in different orders and/or concurrently with other acts or events. Furthermore, not all illustrated acts or events are required to implement a methodology in accordance with the present invention.

Embodiments of the invention may be practiced without the theoretical aspects presented. Moreover, the theoretical aspects are presented with the understanding that Applicants do not seek to be bound by the theory presented.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Expandable Spinal Fusion Device(s)

A spinal fusion is typically employed to eliminate pain caused by the motion of degenerated disk material. Upon successful fusion, a fusion device becomes permanently fixed within the intervertebral disc space.

Referring now to the Figures, the spinal fusion device is inserted into the intervertebral space in the insertion mode to replace damaged, missing or excised disk material. In an exemplary embodiment, the device 10 comprises an upper section 11, a top surface 12, a lower section 13, a bottom surface 14, a body portion 18 and a distractor 55. The device may be made of conventional materials used for surgical implants, such as stainless steel and its many different alloys, titanium, titanium alloys, metallic alloys, polymeric materials, plastics, plastic composites, ceramic and any other metal or material with the requisite strength and biologically inert properties.

In one embodiment, the upper section 11 of the device 10 comprises a top surface 12 for engaging the end plate of a vertebra and the lower section 13 comprises a bottom surface 14 for engaging the end plate of adjacent vertebra. The top surface 12 and bottom surface 14 are planar to provide large contact areas with each vertebra. In other embodiments, the top and bottom surfaces may have sloped edges. In other embodiments, the top surface has a sloped edge. In another embodiment, the bottom surface has a sloped edge. In yet other embodiments, the top and bottom surfaces lack a sloped edge.

The device 10 is hollow, allowing for insertion of bone graft, bone graft material, scaffolds or any tissue or cellular material. In one embodiment, bone graft or similar bone growth inducing material can be introduced around and within the fusion device to further promote and facilitate bone fusion. The fusion device is hollow in the center, further providing a space for packing with bone graft or similar bone growth inducing material. Such bone graft or bone growth inducing material can be packed, prior to, subsequent to, or during implantation of the fusion device.

Figure 4:
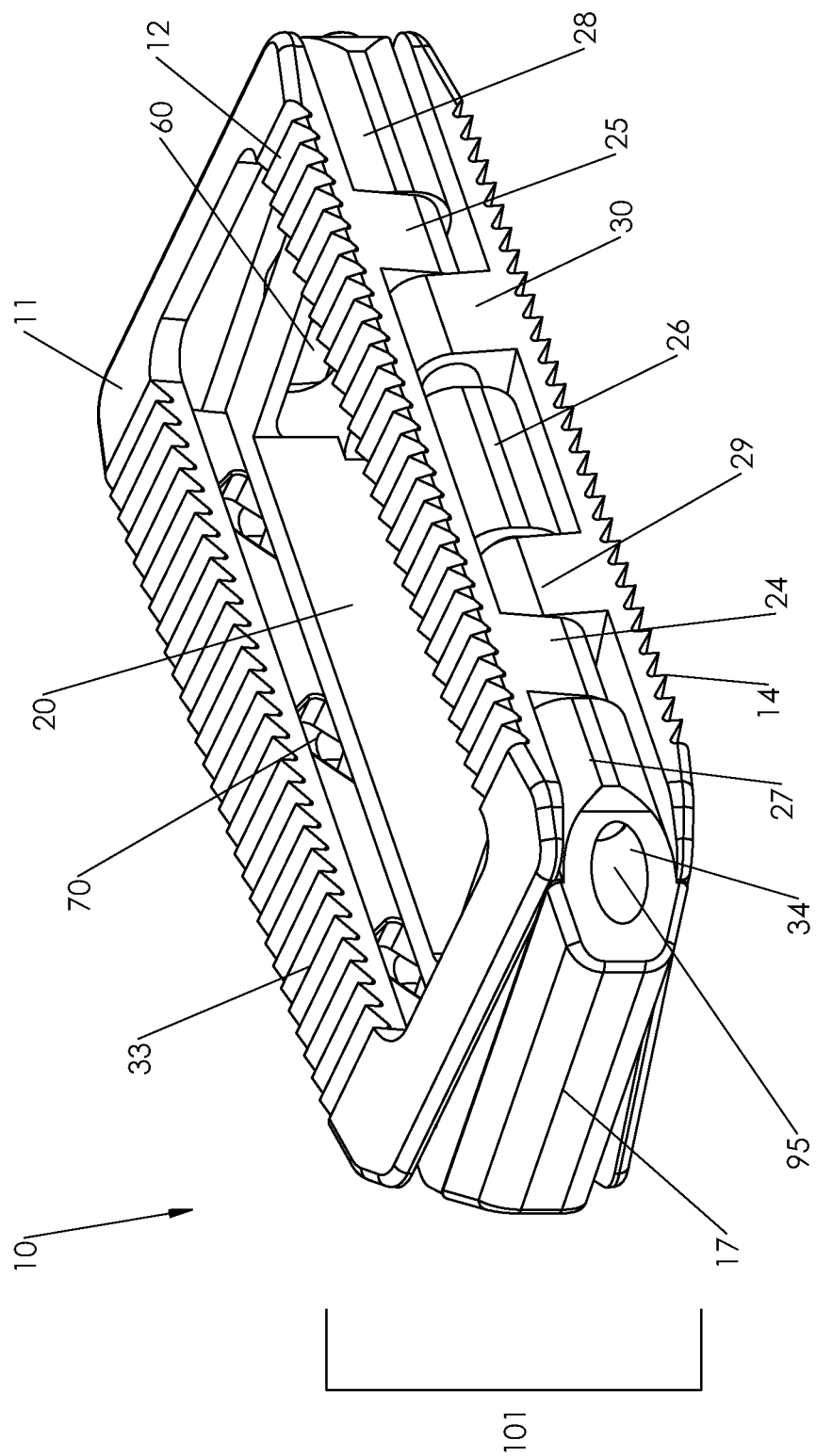
FIG. 4 is a perspective view of the spinal implant in an expanded position.
Figure 5:
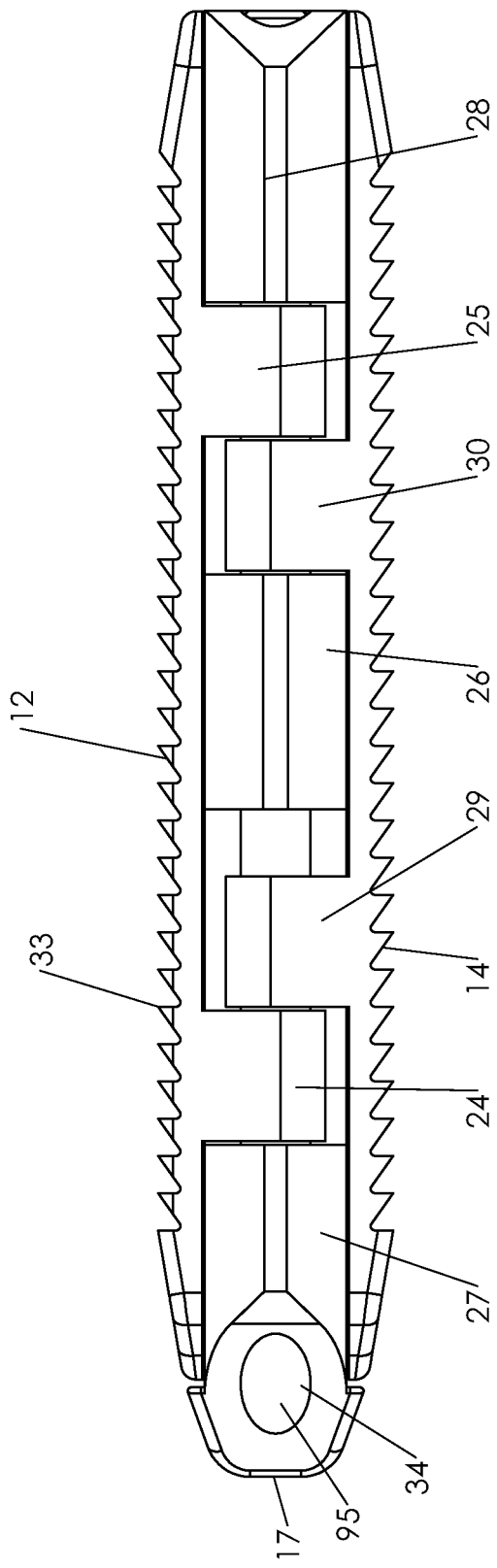
FIG. 5 is a side view of FIG. 4.
Figure 6:
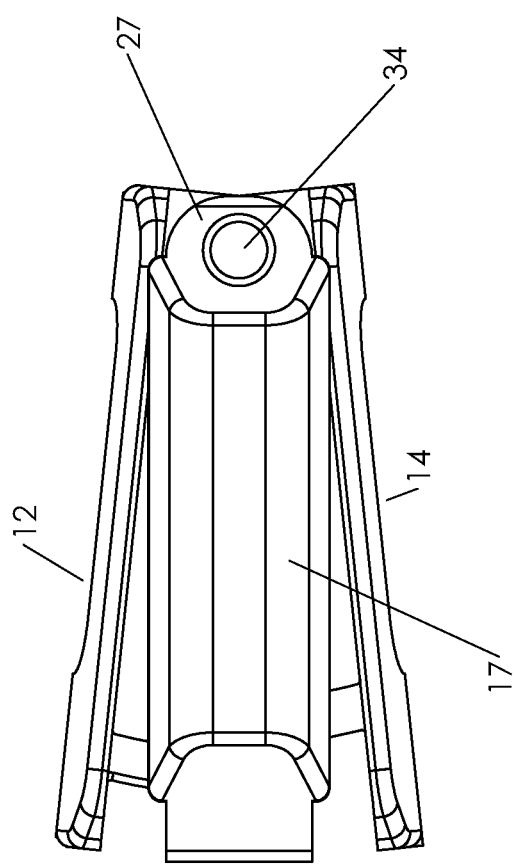
FIG. 6 is an end view of FIG. 5.
Figure 7:
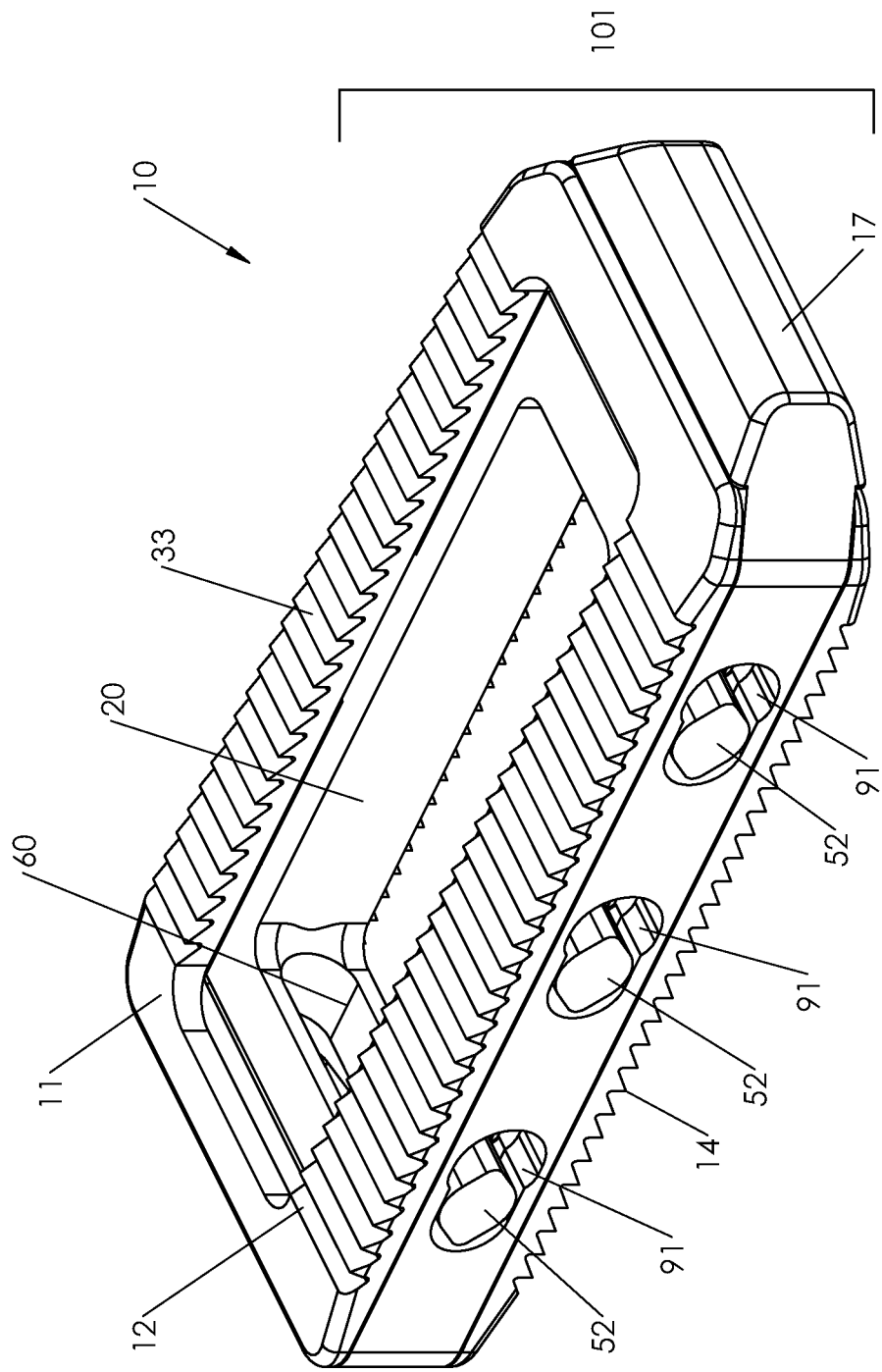
FIG. 7 is a perspective view of the spinal implant in the contracted position.
Figure 8:
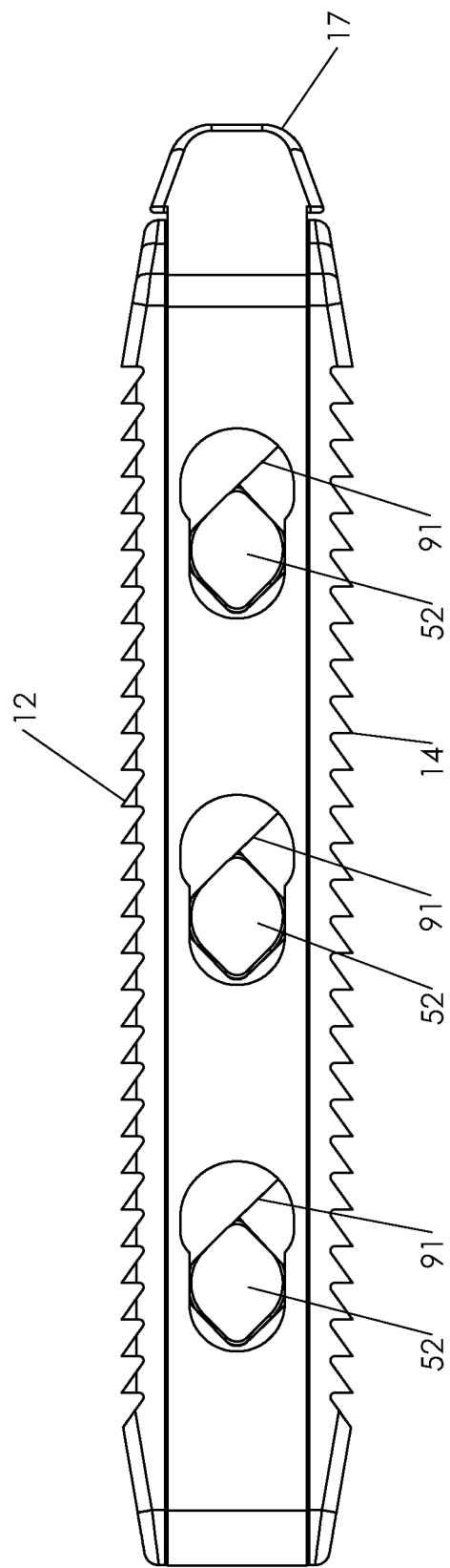
FIG. 8 is a side view of FIG. 7.
Figure 9:
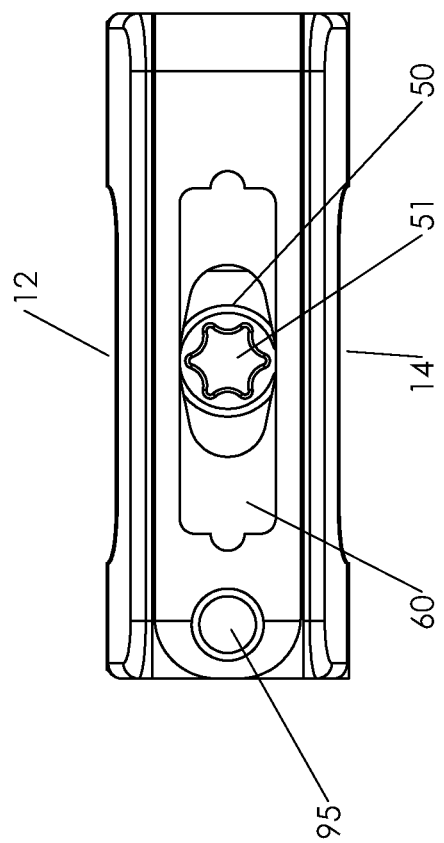
FIG. 9 is an end view of FIG. 7.
Figure 10:
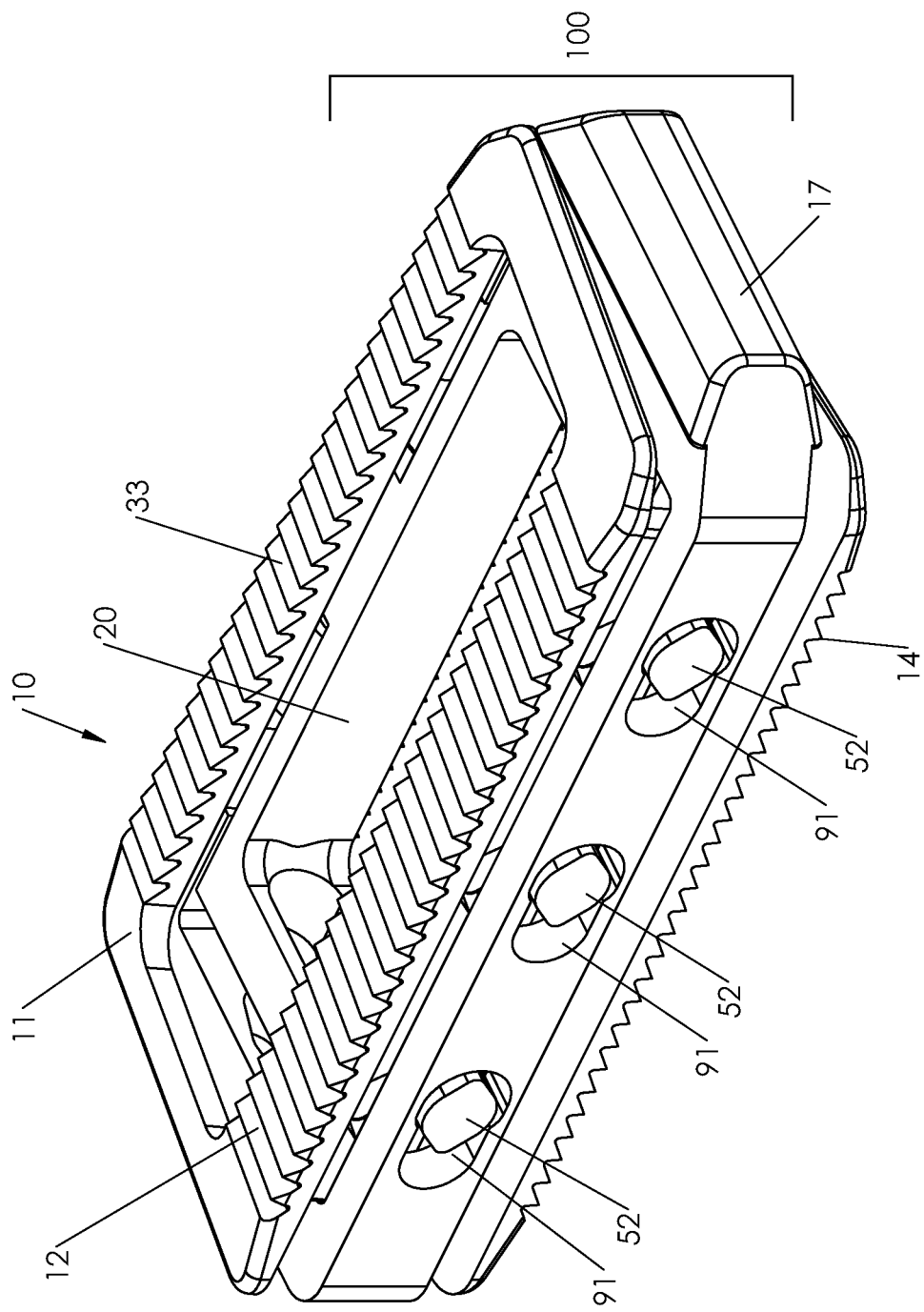
FIG. 10 is a perspective view of the spinal implant in an expanded position.
Figure 11:
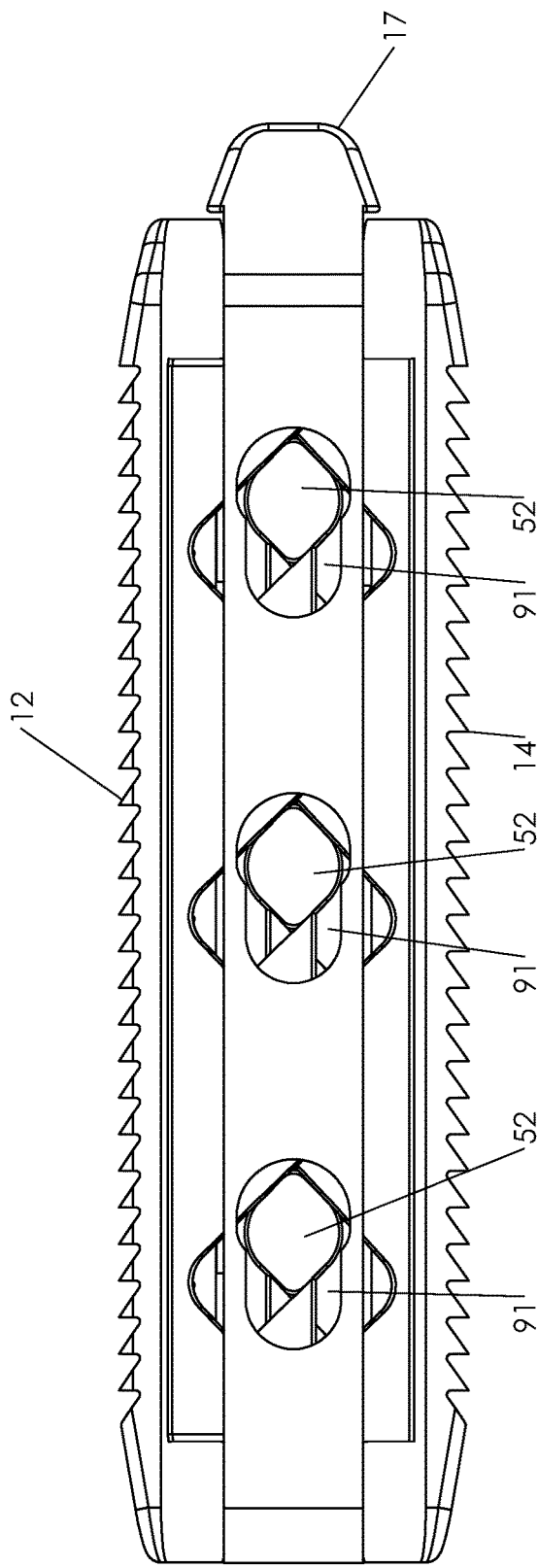
FIG. 11 is a side view of FIG. 10.
Figure 12:
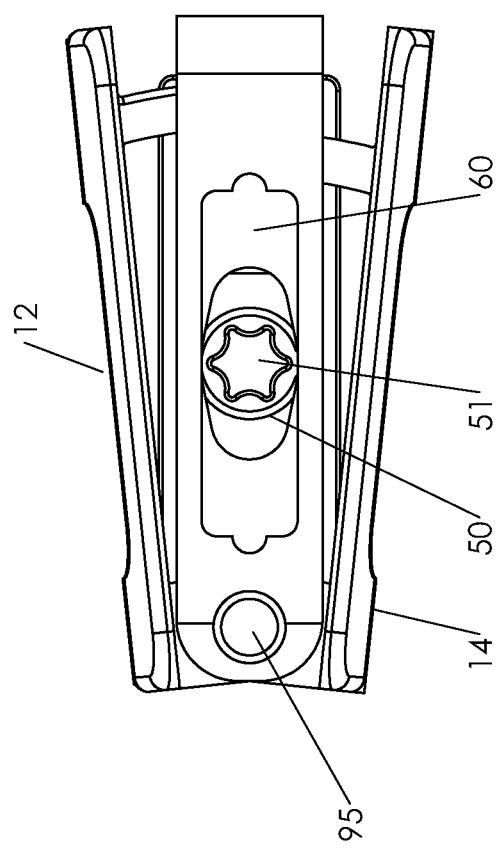
FIG. 12 is an end view of FIG. 10.

The device 10 has two extreme positions and is adjustable infinitely between these positions. In the expanded position 100 (see FIG. 4) the height of the upper section 11 and the lower section 13 are only limited by the pivot assembly 95. The compact position 101 (see FIG. 1) is the height of the body portion 18 and the sum of the thickness of the top surface 12 and bottom surface 14. The top surface 12 and the bottom surface 14 contact the body portion 18 when the device is in a compact or unexpanded position. The device can be rotated along the longitudinal axis 180 degrees so that the upper section becomes the lower section and vice versa.

The upper section 11 comprises a top surface 12 with a large aperture 20 to facilitate bone ingrowth after implantation, and a depending sidewall 23 projecting from the top surface 12 and positioned parallel to at least two joints 24, 25 each having an aperture 31, 32 constructed and arranged to pass through rod 40 to form part of a hinge assembly 95. The depending side walls 23 terminate in a flat plane and side wall possesses at least one slot or groove 70 for engaging a protruding member, rollers or pins 52 of the distractor body 55; the protruding member 52 dimensioned to slidably fit in the slots or grooves 70. The angle of the slot or groove is positioned at a 90° angle relative to the horizontal planar surface of the upper section 11 and can vary so that the maximum expanded position 100 can be increased or decreased. For example, with the groove close to vertical at a 90° angle to the horizontal plane, the maximum expanded position will be greater than if the slot or groove is at a 45° angle relative to the horizontal plane. However, it is to be understood that a slot or groove having, for example, a 45° angle to the horizontal plane would not only expand the upper section 11 vertically, but also displace the distractor 55 horizontally. The slot or groove 70 engages the protruding members 52 of the distractor 55 to guide the relative movement of the upper section 11, maintaining the distractor 55 and the depending sidewall 23 and hinge assembly 95 in alignment.

The bottom surface 14 of the lower section 13 has a large aperture 21 to facilitate bone ingrowth after implantation. The lower section 13 comprises upstanding sidewalls 41 projecting from the bottom surface 14 and positioned parallel to a surface having at least two joints 29, each having apertures 36, 37 constructed and arranged to receive rod 40 to form part of the hinge assembly 95. The distance between the opposing sidewalls 41 is dimensioned to be less than the distance between the opposing sidewall 23 of the upper section 11 so that the upper and lower sections can slidably move between the expanded and compact positions of the device. The depending side wall 41 terminates in a flat plane, and the side wall possesses at least one slot or groove 71 for engaging protruding members 52 of the distractor 55, dimensioned to slidably fit in the slots or grooves 71. The protruding member 52 can be any type, size or shape; for example, rollers, pins, as long as these protruding members 52 can be engaged by the slots or grooves 71. The angle of the slots or grooves 71 of the lower depending side wall 41 relative to the angle of the slots or grooves 70 of the upper depending side wall 23 is greater than 0° and up to 180°. The slots or grooves 70, 71 engage the protruding members, rollers or pins 52 of the distractor 55 to guide the relative movement of the upper and lower sections 11, 13, maintaining the distractor 55 and the depending sidewalls in alignment. The slots or grooves 70, 71 on each opposing sidewall are diametrically opposed on the opposite side walls.

The depending sidewalls of the upper and lower sections and the slot or groove of each sidewall are smooth to provide ease in the relative sliding contact between the sidewalls and between the protruding members 52 of the distractor 55. In alternative embodiments, the slots or grooves 70, 71 may comprise jagged steps, which are positioned to provide a lock-step expansion when the device is expanded.

In the embodiment depicted in FIGS. 1-13, the device 10 comprises a body portion 18, upper and lower sections 11, 13, a distractor 55, and an actuation member 51. The body portion 18 has a first end 17, a second end 19, a first side portion 42 having apertures 91 constructed and arranged to cooperate with protruding members 52 connecting the first end 17 and the second end 19. Attached on the opposite side of the first end 17 and the second end 19 and parallel to first side portion 42 are joints 27, 28 having apertures 34, 35 constructed and arranged to cooperate with insertion of rod 40 to form another part of hinge assembly 95. The first end 17 of the fusion device 10 includes at least one angled surface, a grooved end and a flat end or planar end plate. The first end 17 comprises multiple angled surfaces.

The second end 19 includes an opening 60, which may include threading. The opening 60 is dimensioned to cooperate with a distractor 55. In one exemplary embodiment, the distractor 55 comprises an actuation member 51, a rod 54 and a distractor body 55. The actuation member 51 is located on the outer surface of the second end 19. The rod 54, which extends into the hollow area of the distractor body 55, may be threaded or telescopic for slidably moving the distractor body 55 within the hollow center of the device 10. Although the term "rod" is used, it is merely descriptive and encompasses any shape or form as long as it can move the body of the distractor. In this embodiment, the distractor body 55 is dimensioned to fit in the hollow center of the device and to provide a large volume for the placing of bone graft, bone graft inducing material, scaffolds or any tissue or cellular material. In this embodiment, the rod 54 is attached to the distractor body 55. The distractor body 55 comprises a first end 80, a second end 81, a first side portion 82 connecting the first end 80 to the second end 81, and a second side portion 83 connecting the first end 80 to the second end 81. The first side portion 82 comprises at least one, preferably two protruding members, rollers or pins 52 which are dimensioned to slidably fit into the grooves or slots 70, 71 in the sidewalls of the upper and lower sections. The first end 80, in exemplary embodiments, is a planar surface. In some embodiments, the rod 54 is a jack screw for engagement of a threaded bore 85 at the second end 81 of the distractor body 55.

The distance between the top surface 12 and the bottom surface 14 is adjustable by moving the upper section 11 relative to the lower section 13. The protruding members 52 of the distractor 55 slide downwards when the distractor is actuated and the distance between the upper and lower section decreases. Conversely, the protruding members 52 of the distractor slide upwards when the distractor is actuated and the distance between the upper 11 and lower section 13 increases. The distractor 55 can be a telescopic mechanism, whereby the distractor comprises a member, for example, a telescopic rod, for moving the distractor body 55 by a sliding mechanism and, optionally, a locking mechanism to lock the distractor at a desired position. The distractor is not limited to a sliding mechanism, but can utilize any mechanism as long as the distractor can cause the distractor body 55 to move. In the present embodiment, the distractor body 55 slides upward, causing upper section 11 and lower section 13 to increase relative to the pivot point created by hinge assembly 95.

The device 10 is inserted into the disk space between adjacent vertebrae with the top surface 12 in contact with the end plate of one vertebra and the bottom surface 14 in contact with the end plate of the adjacent vertebra. When the surgeon actuates the distractor, the rod 54 is extended into the cavity, pushing the distractor body 55 and the protruding members 52 to slide along the slots or grooves 70, 71 and pivot about hinge assembly 95, thereby changing the distance between the top and bottom surfaces 12, 14 as the sidewalls move apart, thereby expanding the device 10. When the actuator 51 is actuated in the opposite direction, the rod member 54 retracts, pulling the distractor body 55 towards the end of the outer wall to which the distractor 55 is fastened. The extending of the rod member can be accomplished by a variety of means, including a pushing or pulling mechanism or a rotating mechanism utilizing a screw and thread means. The rod 54 could be telescopic, and in that embodiment, may be comprised of one or more rods of equal and/or varying lengths, each rod having a circumference slightly smaller than the previous rod so that, when the actuator is actuated, the rods can extend beyond the length of the first rod or retract into each other.

The embodiment depicted in FIGS. 1-13 includes a top surface 12 and bottom surface 14 that are constructed with friction teeth 33 for better engagement with the vertebrae. These friction teeth 33 are protrusions that are angled to allow the device 10 to be inserted with a lower resistance, but provide an increased resistance to the device 10 being retracted. This provides for increased stability of the device 10 between adjacent vertebrae. Additionally, the friction teeth 33 may be sloped or angled on the outer edge, as any sharp corner edge can make insertion or proper positioning of the device 10 more difficult.

Figure 13:
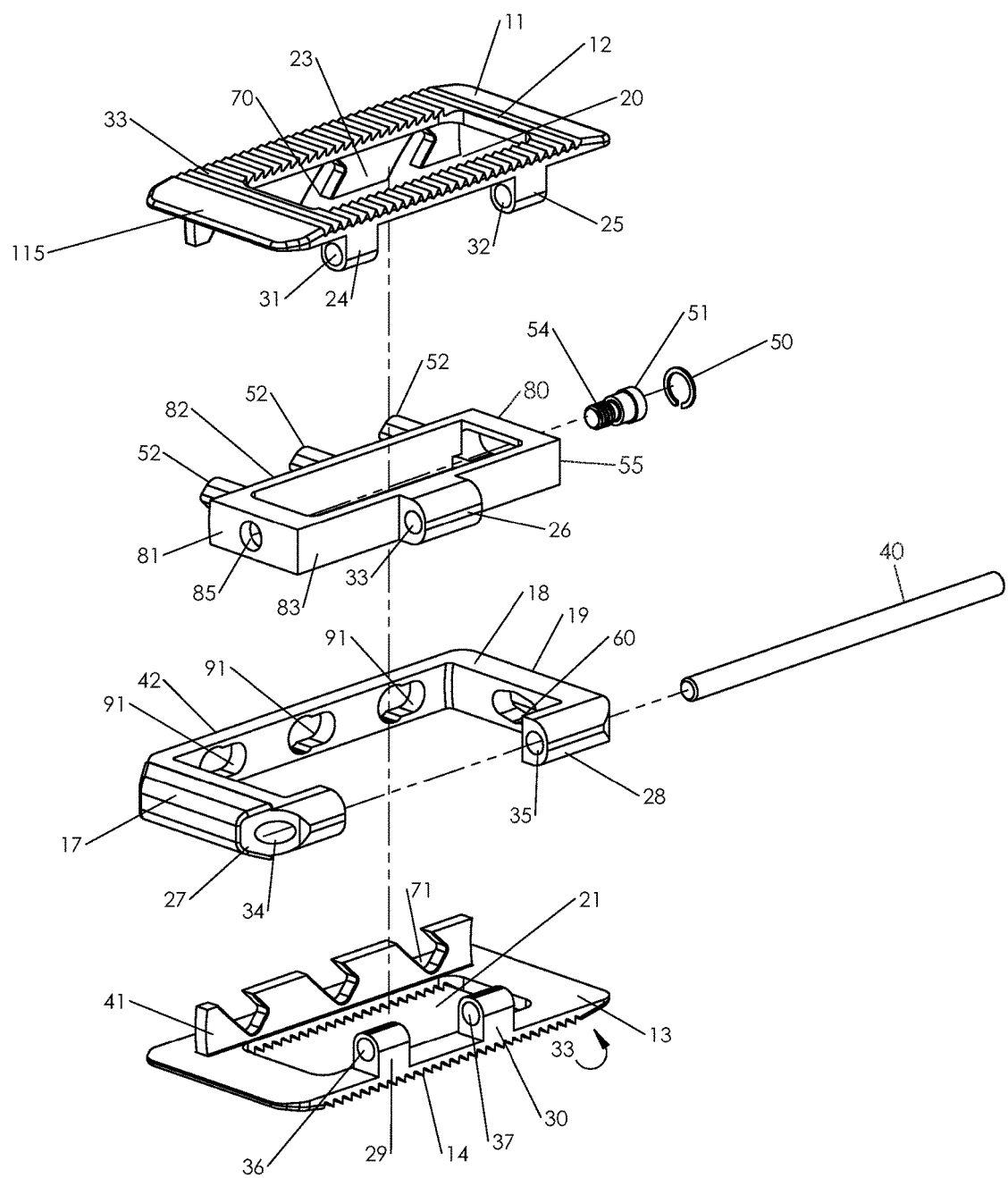
FIG. 13 is an exploded view of the spinal implant with a hinge assembly.

FIG. 13 is an exploded view of a preferred embodiment of the present invention. Device 10 is constructed having an upper section 11 with a top surface 12 and sidewall 23 extending inward and terminating at a plane having slots or grooves 70 to engage with the protruding members 52 of the distractor 55. The top surface 12 has an aperture 20, allowing for a channel to the hollow of the device. There is a sloping or angled leading edge 115 which abuts the first end 17 of the body portion 18 in a compact position 101.

The lower section 13 is constructed to cooperate with the upper section 11, having a bottom surface 14 and sidewall 41 extending inward and terminating at a plane having slots or grooves 71 to engage with the protruding members 52 of the distractor 55. The bottom surface 14 has an aperture 21, allowing for a channel to the hollow of the device. Positioned opposite sidewall 41 are joints 29, 30 having apertures 36, 37 constructed and arranged to cooperate with rod 40, thereby forming part of hinge assembly 95.

In the preferred embodiment, the body portion 18 has apertures 91 on opposing sidewall 42 which act as channels for the protruding members 52 of the distractor 55, which allow the distractor 55 to move along the longitudinal axis of the body portion 18. The opening 60 on the second end 19 of the body portion 18 is enlarged in the preferred embodiment, allowing passage of an actuation member 51 and spacer 50 there through.

The distractor 55 in one embodiment may have an opening on its second end 81, corresponding to the size of opening 60. The openings can create a passage to the hollow, whereby bone graft or similar bone growth material can be inserted into the device 10 and contact the vertebrae on the upper and lower sides of the device 10.

When the device 10 is in a contracted state, the distractor 55 is back towards the second end. The actuation member 51 passes through an opening in the distractor first end 80, then through the spacer 50, and then enters the support aperture 85. The rod 54 of the actuation member 51 is shown here as a jack screw for engagement with the support aperture 79, which includes a bore for receiving the rod 54. The bore is aligned with the opening on the distractor first end.

The device 10 is inserted into the disk space between adjacent vertebrae with the top surface 12 in contact with the end plate of one vertebra and the bottom surface in contact with the end plate of the adjacent vertebra. When the surgeon actuates the distractor, the rod 54 is extended into the aperture 85, pulling the distractor body 55 and the protruding members 52 to slide along the slots or grooves 70, 71 towards the body portion first end 17, thereby changing the distance between the top and bottom surfaces 12, 14 along the hinge assembly 95 as the sidewalls move apart, thereby expanding the device 10. When the actuator 51 is actuated in the opposite direction, the rod member 54 retracts, pushing the distractor body 55 towards the second end 19, and thereby contracting the device. Actuation of the actuation member 51 causes the distractor 55 to move along the longitudinal axis of the body portion 18, guided linearly by the protruding members 52 within apertures 91 of the body portion. This movement along the longitudinal axis of the body portion 18 causes the protruding members 52 to engage with the slots or grooves 70, 71. As the distractor 55 moves from the second end 19 to the first end 17 of the body portion 18, the upper section 11 and lower section 13 are forced apart, rotating about pivot assembly 95, moving perpendicular to the longitudinal axis of the body portion.

The extending of the rod member 54 can be accomplished by a variety of means, including a pushing or pulling mechanism or a rotating mechanism utilizing a screw and thread means. The telescopic rod, in this embodiment, comprises one or more rods of equal and/or varying lengths, each rod having a circumference slightly smaller than the previous rod so that, when the actuator is actuated, the rods can extend beyond the length of the first rod or retract into each other. Passage of an instrument through opening 60 allows a surgeon to actuate the actuation member 51.

In an expanded state of device 10, the friction teeth 33 engage with the adjacent vertebrae to prevent movement of the device 10, now set in place.

Once the device 10 is properly positioned, the tool used for actuation can be removed and bone graft or bone growth material can be inserted through opening 60, where it fills in the hollow of the device and flows outward to the vertebrae through openings in the top surface 12 and the bottom surface 14.

The invention has been described in detail with reference to preferred embodiments thereof. However, it will be appreciated that those skilled in the art, upon consideration of this disclosure, may make modifications and improvements within the spirit and scope of the invention. The following non-limiting examples are illustrative of the invention.

All documents mentioned herein are incorporated herein by reference. All publications and patent documents cited in this application are incorporated by reference for all purposes to the same extent as if each individual publication or patent document were so individually denoted. By their citation of various references in this document, Applicants do not admit any particular reference is "prior art" to their invention.

What is claimed is:

1. A spinal fusion device for implanting or placing between adjacent vertebrae comprising:
   a hollow body having an upper section with a top surface for contacting one vertebra and a lower section having a bottom surface for contacting an adjacent vertebra, said top surface and said bottom surface constructed and arranged for engaging the vertebra, each section having a depending sidewall opposite at least one joint having an aperture, said at least one joint constructed and arranged to receive a rod thereby forming a pivot assembly, a top sidewall being slidably mounted over a bottom sidewall, each sidewall constructed and arranged for engaging a distractor, positioned between said upper section and said lower section is a hollow body section,
   said hollow body section having a first end comprising an angled surface and a second end comprising an opening for disposing of a distractor; said hollow body section having at least one joint having an aperture constructed and arranged to receive said rod, said hollow body constructed and arranged for receipt of bone graft material.

2. The spinal fusion device of claim 1, wherein the distractor comprises:
   an actuator at one end of an elongated member disposed through the opening of the end of the hollow body section,
   a distractor body comprising protruding members, wherein the protruding members are engaged by slots or grooves in the sidewalls of the upper and lower sections, whereby the distance between the top and bottom surfaces is adjustable as the protruding members of the distractor body move within the slots or grooves, thereby moving the upper section relative to the lower section.

3. The spinal fusion device of claim 2, wherein the elongated member comprises threading for slidably moving the distractor body.

4. The spinal fusion device of claim 1, wherein the opening on the first end of the body section of the device further comprises threads for engaging the rod member of the distractor and is aligned with an opening in the distractor body for receiving the elongated member and to move the distractor body relative to the depending sidewalls as the actuator is threaded into the opening in the first end of the body section of the device.

5. The spinal fusion device of claim 1, wherein the depending sidewalls comprise a slot or groove for engaging the protruding members of the distractor body, which are dimensioned to slidably fit into the slot or groove, whereby the distance between the bottom surface and the top surface is adjustable by moving the upper section relative to the lower section.

6. The spinal fusion device of claim 5, wherein the protruding members of the distractor body slidably move in the slots or grooves in a first direction when the distractor is actuated and the distance between the upper and lower section decreases, or, the protruding members of the bracket move in the slots or grooves in a second direction opposite to the first direction when the distractor is actuated and the distance between the upper and lower section increases.

7. The spinal fusion device of claim 6, wherein, upon the distractor slidably moving in the second direction, the upper and lower sections increase unevenly to form a substantially wedge shape.

8. The spinal fusion device of claim 6, wherein the top and bottom surfaces are substantially convex.

9. The spinal fusion device of claim 1, wherein the first end of the body section comprises at least one angled surface.

10. The spinal fusion device of claim 1, wherein the means for engaging the vertebra comprises a plurality of angled surfaces sloping towards the first end.

11. The spinal fusion device of claim 1, wherein the hollow body is dimensioned to fit bone or bone graft material.

12. A spinal fusion device for adjusting the space between vertebrae comprising:

a hollow body having an upper section with a top surface for contacting one vertebra and a lower section having a bottom surface for contacting an adjacent vertebra, said top surface and said bottom surface constructed and arranged for engaging the vertebra, each section having a depending sidewall opposite at least one joint having an aperture, said at least one joint constructed and arranged to receive a rod, thereby forming a pivot assembly, the top sidewall being slidably mounted over the bottom sidewall, each sidewall having a slot or groove for engaging a distractor, said sidewalls surrounded by a hollow body section comprising a first end having angled surfaces and a second end having an opening for disposing of the distractor, said hollow body section having at least one joint having an aperture constructed and arranged to receive said rod, said hollow body constructed and arranged for receipt of bone graft material.

13. The spinal fusion device of claim 12, wherein the distractor comprises a body disposed in the hollow body, said distractor having at least one joint with an aperture constructed and arranged to receive said rod of said pivot assembly.

14. The spinal fusion device of claim 12, wherein the distractor comprises a threaded rod attached to an actuator for adjusting the distractor, whereby the distance between the top and bottom surfaces is adjustable by moving the upper section relative to the lower section along said pivot assembly, the upper and lower section depending side walls are comprised of slots for engaging protruding members of the distractor body, wherein the protruding members are dimensioned to fit into the sidewall slots for slidably moving the top and bottom surfaces, thereby opening said device about said pivot assembly.

15. The spinal fusion device of claim 14, wherein the distractor further comprising a bore, a jack screw in the bore threaded into the rod whereby the distractor moves relative to the bottom surface as the jack screw is threaded into the distractor body.

16. The spinal fusion device of claim 14, wherein the distance between the top and bottom surfaces increases unevenly to form a substantially wedge shape, angled towards the first end.

17. The spinal fusion device of claim 12, wherein the top and bottom surfaces are substantially convex.

18. The spinal fusion device of claim 12, wherein the upper and lower sections further comprise a plurality of sloped or angled protruding surfaces for frictionally engaging a vertebra.

19. The spinal fusion device of claim 12, wherein the hollow body is dimensioned to fit bone or bone graft material.

* * * * *